(12) United States Patent
Kutscher et al.

(10) Patent No.: US 7,760,928 B2
(45) Date of Patent: Jul. 20, 2010

(54) FOCUS ERROR CORRECTION SYSTEM AND METHOD

(75) Inventors: Tuvia-Dror Kutscher, Shoham (IL); Yaacov Zak, Meitar (IL); Rami Elishai, Ashqelon (IL); Erez Fridman, Tel Aviv (IL)

(73) Assignee: Applied Materials Israel, Ltd., Rehovot (IL)

( * ) Notice: Subject to any disclaimer, the term of this patent is extended or adjusted under 35 U.S.C. 154(b) by 946 days.

(21) Appl. No.: 11/550,357

(22) Filed: Oct. 17, 2006

(65) Prior Publication Data

US 2008/0089617 A1     Apr. 17, 2008

(51) Int. Cl.
*G06K 9/03* (2006.01)
(52) U.S. Cl. ..................... 382/145; 382/255
(58) Field of Classification Search .......... 382/141, 382/255, 145; 356/609; 396/80, 79, 82, 396/121; 348/208.12, 345, 349, 350
See application file for complete search history.

(56) References Cited

U.S. PATENT DOCUMENTS

| | | | | |
|---|---|---|---|---|
| 4,540,278 | A * | 9/1985 | Phillips | 355/55 |
| 7,145,846 | B2 * | 12/2006 | Ando | 369/44.26 |
| 2007/0041003 | A1 * | 2/2007 | Ausschnitt et al. | 355/55 |
| 2008/0212457 | A1 * | 9/2008 | Bruls et al. | 369/275.1 |

* cited by examiner

*Primary Examiner*—Jon Chang
(74) *Attorney, Agent, or Firm*—Sonnenschein Nath & Rosenthal LLP

(57) ABSTRACT

A method for focus error corrections. The method includes: determining a focus scheme in response to: a spatial relationship between an upper surface of at least a first portion of a substantially transparent upper layer of an inspected object and between an upper surface of at least a first portion of a reflective layer of the inspected object; wherein the reflective layer is positioned below the transparent upper layer, and a position of at least one height differentiated narrow feature of inspected object; wherein during a scan of each height differentiated narrow feature a focus error signal change rate well exceeds a focus correction rate of a focus error correction unit; and applying the focus scheme while scanning at least a portion of the inspected object.

20 Claims, 6 Drawing Sheets

Determining a focus scheme in response to: (i) a spatial relationship between an upper surface of at least a first portion of a substantially transparent upper layer of an inspected object and between an upper surface of at least a first portion of a reflective layer of the inspected object and (ii) a position of at least one height differentiated narrow feature of inspected object. The reflective layer is positioned below the transparent upper layer and during a scan of each height differentiated narrow feature a focus error signal change rate well exceeds a focus correction rate of a focus error correction unit. 310

Applying the focus scheme while scanning at least a portion of the inspected object. 350

300

FOCUS ERROR CORRECTION SYSTEM AND METHOD

FIELD OF THE INVENTION

The present invention relates to a system having focus error correction capabilities and a method for focus correction.

BACKGROUND

Focus correction systems and methods are aimed to minimize (and even reduce to zero) focus errors. Light based focus error correction systems illuminate an inspected object, receive light reflected from the inspected object and determine a focus error based upon the spatial relationship between images that are imaged on an imaging sensor. The spatial relationship is translated to a focus error correction signal that is fed to a motor that can mechanically move the inspected object such as to ideally minimize (and even cancel) the focus error.

Due to the high accuracy required from the motor, as well as due to mechanical limitations, the motor is characterized by a relatively long response period. This long response period can well exceed the scanning period of height differentiated narrow features of the inspected object. Accordingly, a focus, error correction unit is not able to properly compensate for height differences between the height differentiated narrow features and their surroundings.

In addition, many inspected objects (including many integrated circuits) include a relatively transparent layer (such as a Copper Mechanical Polish layer) that is positioned above a highly reflective layer (such as a copper layer). When such inspected objects are illuminated with a light beam, most of the reflected light will originate from the highly reflective layer and the focus error signal will mainly represent the upper surface of the highly reflective layer and not the upper surface of the inspected object. By minimizing (and even canceling) the focus error signal the focus error correction unit focuses on the highly reflective layer and the surface of the inspected object will be out of focus.

There is a need to provide efficient methods for focus error corrections and efficient systems having focus error correction capabilities.

SUMMARY OF THE INVENTION

A method for focus error corrections. The method includes: (i) determining a focus scheme in response to: (a) a spatial relationship between an upper surface of at least a first portion of a substantially transparent upper layer of an inspected object and between an upper surface of at least a first portion of a reflective layer of the inspected object; wherein the reflective layer is positioned below the transparent upper layer, and (b) a position of at least one height differentiated narrow feature of inspected object; wherein during a scan of each height differentiated narrow feature a focus error signal change rate well exceeds a focus correction rate of a focus error correction unit; and (ii) applying the focus scheme while scanning at least a portion of the inspected object.

A system having focus error corrections capabilities, the system includes a controller and a scanner. The controller is adapted to determine a focus scheme in response to: (a) a spatial relationship between an upper surface of at least a first portion of a substantially transparent upper layer of an inspected object and between an upper surface of at least a first portion of a reflective layer of the inspected object; wherein the reflective layer is positioned below the transparent upper layer, and (b) a position of at least one height differentiated narrow feature of the inspected object; wherein during a scan of each height differentiated narrow feature a focus error signal change rate well exceeds a focus correction rate of a focus error correction unit of the system; and wherein the controller is adapted to apply the focus scheme while the scanner scans at least a portion of the inspected object.

DETAILED DESCRIPTION OF THE INVENTION

The following detailed description is of exemplary embodiments of the invention but the invention is not limited thereto, as modifications and supplemental structures may be added, as would be apparent to those skilled in the art.

Figure 1:
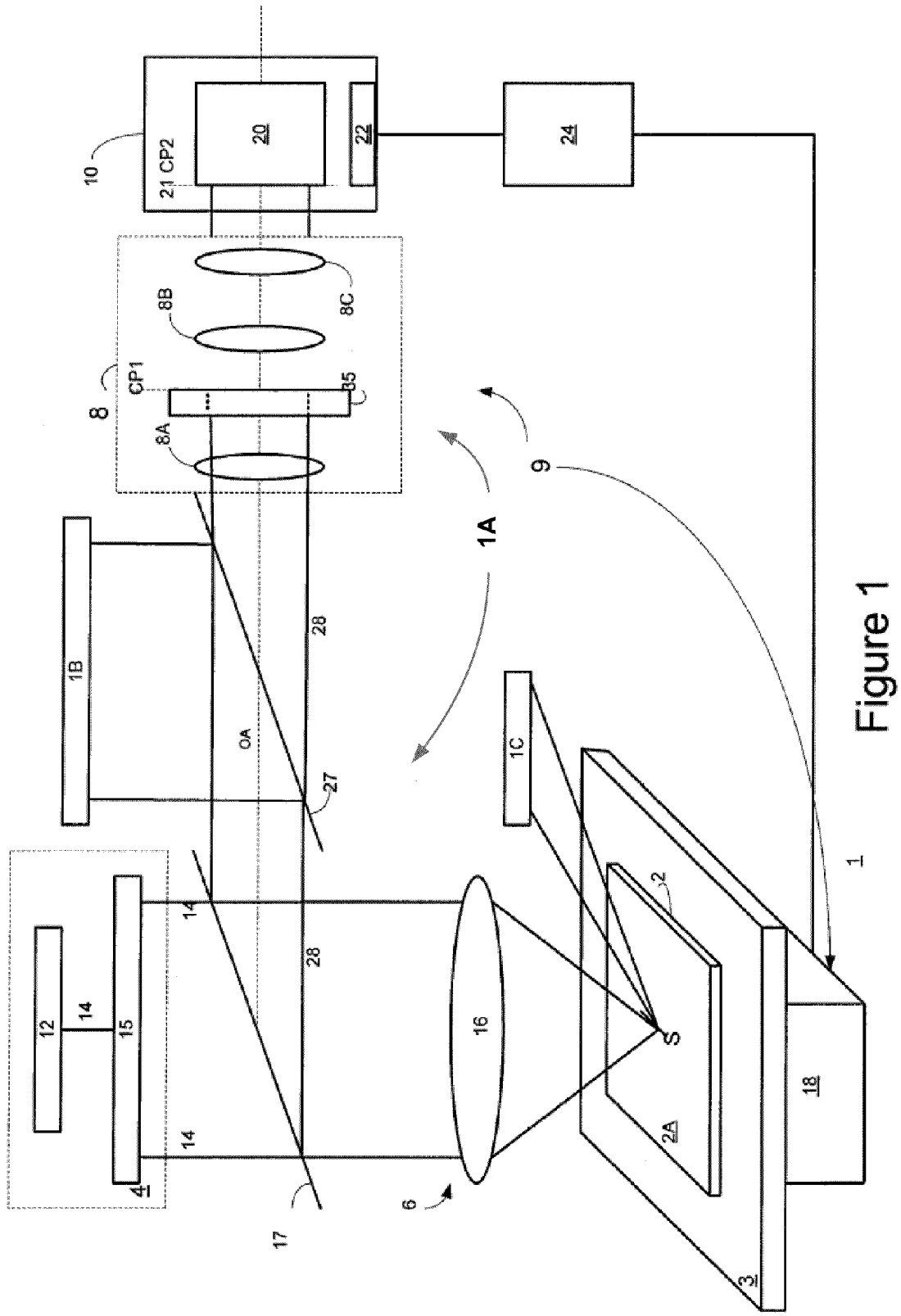
FIG. 1 illustrates a schematic representation of a system according to an embodiment of the invention.
Figure 2:
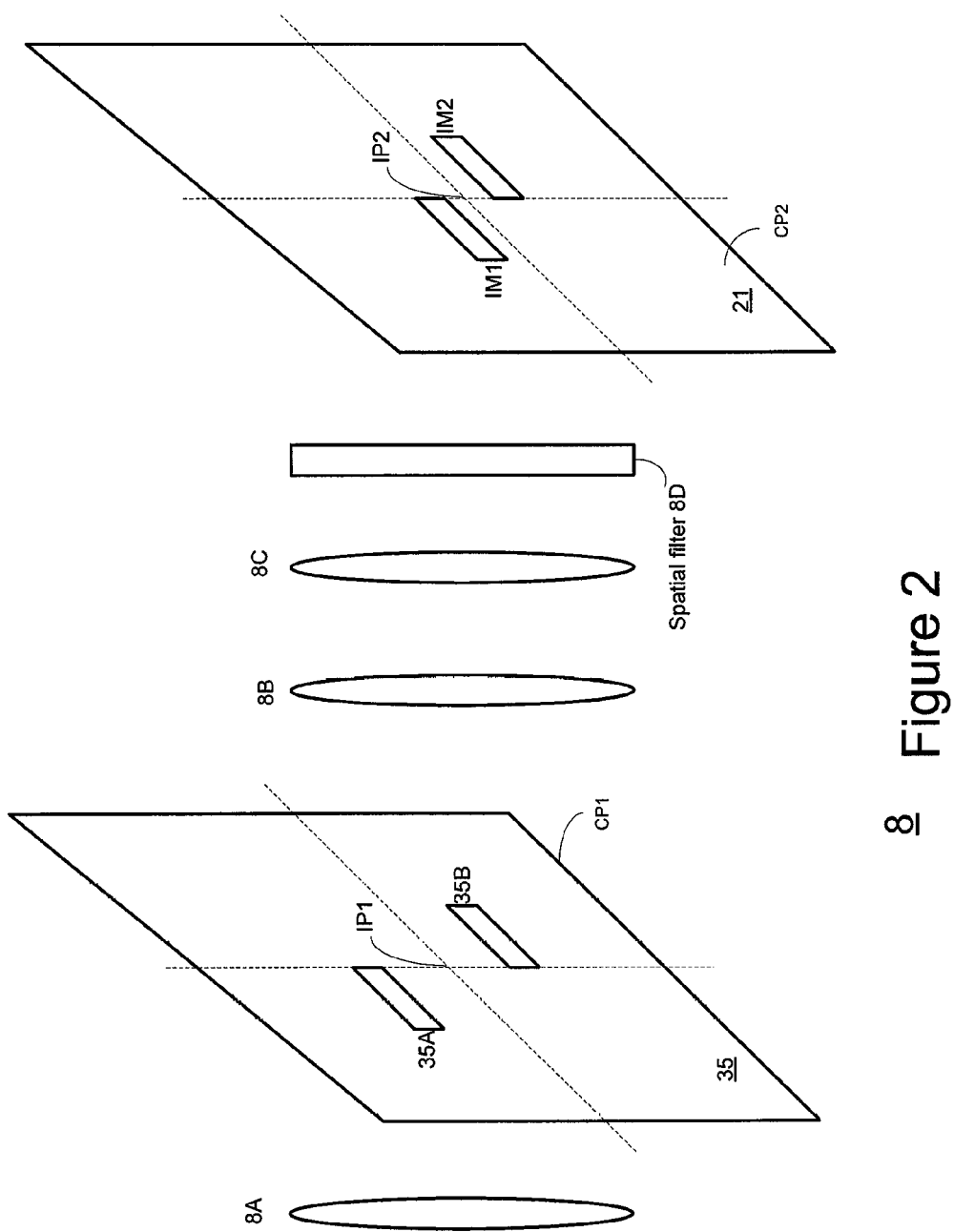
FIG. 2 illustrates in greater detail imaging optics and an image formed on a detector, according to an embodiment of the invention.

FIG. 1 illustrates an inspection system 1 having focus error correction capabilities. FIG. 2 illustrates in greater detail imaging optics 8 and an image formed on detector 20, according to an embodiment of the invention.

Figure 4:
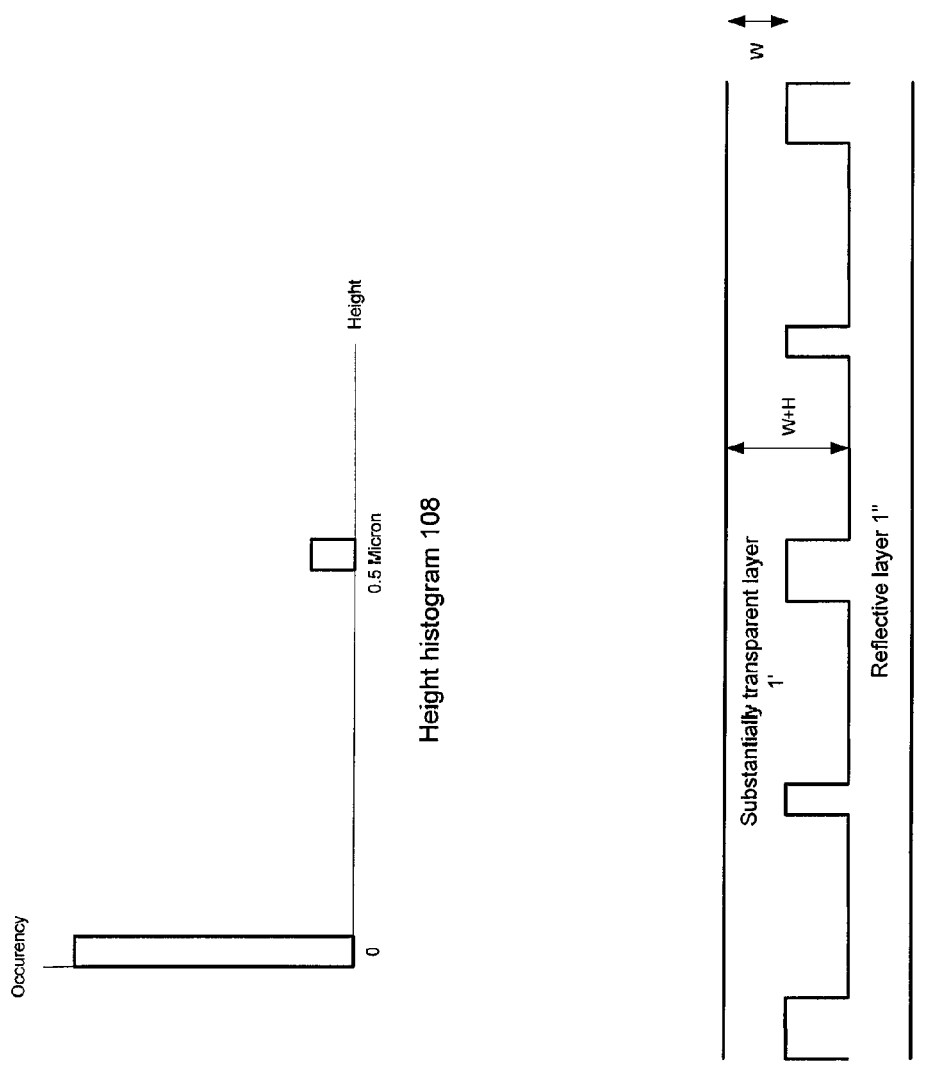
FIG. 4 illustrates a cross section of a portion of the inspected object and a height histogram of a slice, according to an embodiment of the invention.

System 1 is illustrated as inspecting an inspected object such as wafer 2. Wafer 2 includes a substantially transparent layer that is positioned above a reflective layer. FIG. 4 illustrates substantially transparent layer 1' that is positioned above reflective layer 1". While substantially transparent layer 1' is relatively flat, reflective layer 1" usually includes patterns that are characterized by different heights. It is noted that reflective layer 1" can include height differentiated narrow features although this is not necessarily so and height differentiated narrow features can belong to other layers of wafer 2. Scribe lines usually belong to another layer of wafer 2.

System 1 includes optics 1A, a bright-field detection unit 1B and a dark-field detection unit 1C. Wafer 2 is typically located on a support stage 3 translating wafer 2 within an inspection plane. The construction and operation of the detection units 1B and 1C do not form the part of the present invention and therefore need not be specifically described except to note the following. The dark-field detection unit 1C includes a suitable detector and an appropriately oriented collecting optics, while the bright field detection unit 1B includes a charge coupled device (CCD) camera (not shown) receiving a part of returned radiation collected with the optics 1A, as will be described more specifically further below. It is noted that system 1 can include only bright-field detection units or only dark-field detection units, and can apply various illumination and collection techniques (including oblique illumination and normal illumination), known in the art.

Optics 1A includes illumination unit (also referred to scanner) 4, focusing-collecting optics 6, imaging optics 8 and detection unit 10. Illumination unit 4 includes laser source 12 emitting an incident beam 14, and a deflector 15 which may be an acousto-optic element, a mirror, or the like, causing incident beam 14 to scan along wafer 2. It should be noted that a linear beam could be used for the same purpose, i.e. for illuminating an elongated region on wafer 2.

Focusing-collecting optics 6 is typically an objective lens 16 (or a plurality of such lenses). Objective lens 16 focuses deflected beam 14 onto a scan line S (constituting the elongated region) on wafer 2.

Motor 18 is connected to stage 3 for driving a reciprocating movement of the stage along vertical axis or an optical axis of objective lens 16 to change the position of its focal plane P relative to surface 2A of wafer 2. Alternatively or additionally, a similar motor may be associated with objective lens 16.

Further provided is a beam splitter 17 that separates the incident and returned radiation and directs the returned radiation towards detection unit 10. According to the present example, the beam splitter 17 is in the form of a partially transparent mirror that transmits and reflects radiation impinging thereon from two opposite directions, respectively, namely transmits the incident radiation and reflects the returned radiation. Alternatively, a polarizing beam splitter equipped with phase-shifting plates may be used.

Detection unit 10 includes detector 20, for example a charge coupled device (CCD) camera having a plurality of sensing elements (not shown) that typically detect light signals and generate electrical output representative thereof, to be transmitted through output circuit 22. The sensing elements define together sensing surface 21. The CCD camera could be replaced by a position sensitive detector.

Interconnected between motor 18 and the output circuit 22 is a controller 24. Controller 24 receives focus error signals and determines focus error correction signals to be sent to motor 18. Controller 24 can also determine a focus scheme and apply the focus scheme during the scanning of wafer 2.

Focus error correction unit 9 includes motor 18, detection unit 10 and controller 24. This unit can form a feedback loop that can close and open the feedback loop according to the locations of height differentiated narrow features of wafer 2.

System 1 also includes beam splitter 27 accommodated in the optical path of the collected returned light reflected from mirror 17. Beam splitter 27 is a semi-transparent mirror that partly transmits and partly reflects radiation impinging thereon. Hence, the mirror 27 reflects a part of the collected radiation towards detection unit 1B, while transmitting the other part of the collected radiation towards the imaging optics 8.

Optics 1A operates in the following manner. Incident beam 14 propagates through beam splitter 17 and objective lens 16, and illuminates line S, while being focused onto an imaginary focal plane P, which may occasionally not coincide with surface 2A. Typically, the light is mainly reflected from the upper surface of reflective layer 1" and not from surface 2a, thus the focus error signals obtained in focus error collection unit represent the height of the reflective layer 1".

The beams' propagation is shown here schematically to facilitate the illustration of the main components and operational principles of optics 1A. Light portion, generally at 28, mainly returned (reflected) from the upper surface of reflective layer 1", is collected by lens 16. Objective lens 16 constitutes an aperture stop that defines the collected light portion 28. The collected light 28 is reflected to the mirror 27, which allows the transmission of the part of collected light 28 towards detection unit 10 through imaging optics 8, and reflects the other part of collected light 28 towards detection unit 1B.

Imaging optic 8 forms images indicative of the position of an upper surface of reflective layer 1" relative to the imaginary focal plane P on the sensing surface 21, as will be described more specifically further below.

FIG. 2 illustrates in greater details imaging optics 8. Imaging optics 8 includes three different lens arrangements 8A-8C that define a common optical axis OA and plate 35 interposed between lens arrangements 8A and 8C. Plate 35 is oriented perpendicular to the common optical axis OA. Plate 35 is formed with a pair of slits 35A and 35B representing two transmitting regions surrounded by blocking regions of the plate. The slits pick out two light components from light impinging onto plate 35 and transmit them towards the lens arrangement 8B. The slits 35A and 35B are identical in the shape and dimensions and are centrally symmetrical relative to an intersection point IP1 between plate 35 and common optical axis OA, the purpose of which will be explained further below.

Generally speaking, lens arrangement 8A, in combination with beam splitter 17, represents a translation matrix to move image formation away from optical interfaces defined by the focusing optics 6. Lens arrangement 8A includes two lenses that operate in a telescopic mode to form a magnified image of the aperture stop defined by objective lens 16 in plane CP1. The image magnification is required to adapt the size of the aperture stop to sensing surface 21 of the CCD camera 20.

Light that passes through slits 35A and 35B is in the form of two components 28A and 28B. These light components impinge onto lens arrangement 8B. The latter includes a spherical lens (or plurality of such lenses), the sensing surface 21 being disposed in a focal plane of lens arrangement 8B. The spherical lens forms an image of the scan line S along the Y-axis in its focal plane. The X-, Y and Z-axes extend, respectively, along the scan line S, perpendicular to the scan line, and along common optical axis OA.

Lens arrangement 8C includes an appropriate number of cylindrical lenses, two in the present example that operate together for forming an image of the slits 35A and 35B in a plane CP2, which is conjugate to the plane CP0 along the X-axis, i.e. parallel to the scan line S. The CCD camera 20 is located such that its sensing surface 21 is positioned in plane CP2. The slits' image along the X-axis is magnified in order to be projected onto the entire sensing surface 21.

It is noted that the imaging optics as well as other components of system can resemble any system out of the systems illustrated in U.S. Pat. Nos. 6,124,924 and 6,750,436 of Feldman et al., which are incorporated herein by reference.

Thus, two images IM1 and IM2 are obtained on the sensing surface 21 of the CCD camera, actuating corresponding sensing elements, each representing a pixel of the image. Each of the images is formed by a corresponding one of the light components 28A and 28B, picked out by the respective slit.

Each of the images IM1 and IM2 is in the form of an elongated region extending along the X and Y axes, representing the slit image projection along the X-axis and the scan line image projection along the Y-axis. When the scan line S is located in the focal plane P of objective lens 16 (i.e. the aperture stop), the images IM1 and IM2 are merged into a line, while being spatially separated when in any out-of-focus position of the scan line S. Moreover, the images are centrally symmetrical relative to the intersection point IP, and are spaced from each other along two mutually perpendicular axes.

The relative position of IM1 and IM2 indicate the focus error of system 1, especially the height difference between an illuminated point of reflective layer 1" and objective lens 16.

Controller 24 receives information representative of the location of these images (IM1 and IM2), and in response determine what is the focus error. Accordingly, these signals can be regarded as focus error signals.

The controller 24 can determine how to respond to these focus error signals and can, when necessary, send focus error correction signals to motor 18.

Conveniently, controller 24 can determine a focus scheme and then apply it. The focus scheme is determined in response to: (i) a spatial relationship between an upper surface of at least a first portion of a substantially transparent upper layer of an inspected object and between an upper surface of at least a first portion of a reflective layer of the inspected object; wherein the reflective layer is positioned below the transparent upper layer, and (ii) a position of at least one height differentiated narrow feature of the inspected object; wherein during a scan of each height differentiated narrow feature a focus error signal change rate well exceeds a focus correction rate of a focus error correction unit of the system.

Controller 24 is adapted to apply the focus scheme while scanner 4 scans at least a portion of the inspected object.

Conveniently, controller 24 is adapted to ignore focus error signals generated while when scanner 4 scans at least one height differentiated narrow feature.

Conveniently, controller 24 is adapted to determine focus error correction signals, when scanner 4 scans a height differentiated narrow feature, in response to focus error signals obtained from an area proximate to the height differentiated narrow feature.

Conveniently, controller 24 is adapted to determine focus error correction signals, when the scanner scans a height differentiated narrow feature, in response to an expected shape of the height differentiated narrow feature.

Conveniently, controller 24 is adapted to determine target focus error signals at multiple locations, in response to spatial relationships between the substantially transparent upper layer and the reflective layer at these multiple locations.

Conveniently, system 1 is adapted to determine a focus scheme by repetitively scanning a first portion of the substantially transparent upper layer and a first portion of the reflective layer and to define, at multiple locations, target focus error signals that differ from zero.

Conveniently, system 1 includes spatial filter 8D (as illustrated in FIG. 2) that is adapted to selectively mask light reflected from at least a portion of a height differentiated narrow feature, before reaching the focus error correction unit. Spatial filter 8D can form a part of imaging optics 8. It may be positioned in any location that will easily enable to fit the shape of the filtered zone to the shape of the feature or a portion of the feature that should be masked. This masking allows to track after the well defined area.

Conveniently, system 1 is adapted to scan multiple areas of the inspected object and generate reflected layer height statistics representative of the distribution of heights of multiple locations of each area. These areas can be shaped as slices but this is not necessarily so.

Conveniently, controller 25 is further adapted to define at least one feature as a height differentiated narrow feature in response to the statistics.

Conveniently, controller 24 is adapted to convert a first focus error correction map that comprises pixels of a first size to a second focus error correction map that comprises pixels of a second size. The converting is responsive to a relationship between the first size and the second size and to a relationship between a reflectivity of the height differentiated narrow feature and a reflectivity of a surroundings of the height differentiated narrow feature.

It is noted the focus error correction map can be provided or generated by other means, such as previous measurements of the inspected object.

Figure 3:
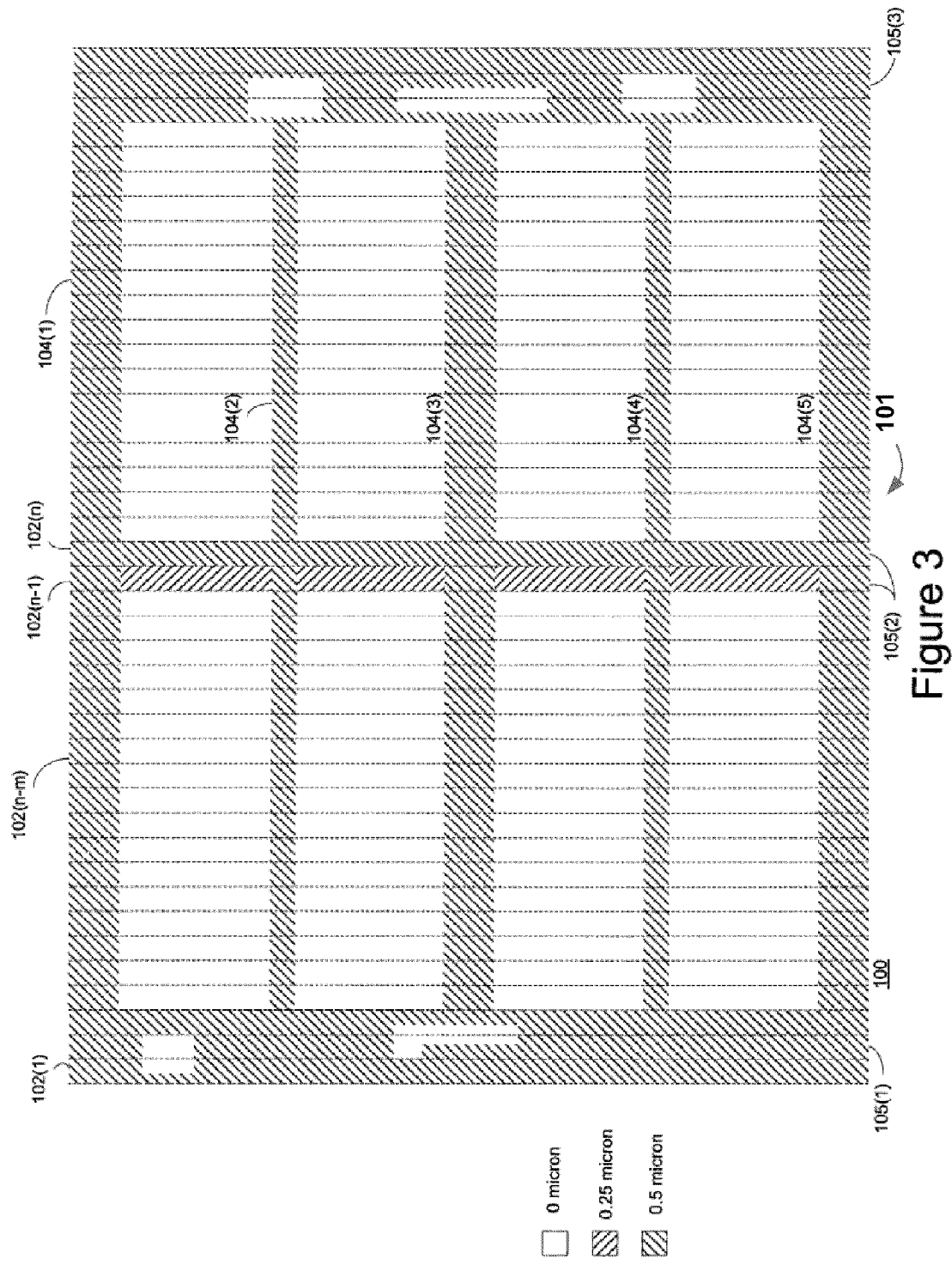
FIG. 3 illustrates an exemplary height map of a portion of a reflective layer, a cross section of the portion and a height histogram of a slice, according to an embodiment of the invention.

FIG. 3 illustrates an exemplary height map 100 of a portion of reflective layer 1", according to an embodiment of the invention. FIG. 4 illustrates a cross section 170 of the same portion of reflective layer 1", and a height histogram 180 of slice 102($n$-$m$).

The portion is a DRAM memory die. It includes substantially transparent layer 1' as well as reflective layer 1" positioned below the substantially transparent layer F. Height map 100 represents the surface of the substantially transparent layer 1' while cross section 170 illustrates both layers.

Portion 101 and especially reflective layer 1" includes eight memory cell "boxes", each "box" includes many memory cells, that are surrounded by five narrow horizontal stitches 104(1)-104(5) that are much higher (about 0.5 micron higher) then their surroundings. It is noted that the stitches can be regarded as belonging to yet another layer of portion 101.

The height map 100 was generated by a scanning pattern that includes vertical scan lines (also referred to as slices) 102(1)-102(2$n$). A narrow vertical stitch 105(2) is positioned at the middle of portion 101. Two relatively wide vertical stitches 105(1) and 105(3) are positioned at both sides of portion 101.

Height histogram 108 of slice 102($n$-$m$) illustrates that the most common height is 0 micron, which is the height of each memory cell "box" and the less frequent height is a height of 0.5 micron—the height of narrow horizontal stitches 104(1)-104(5).

It is noted that a height histogram of slices 101(1) and 102(2$n$) that scan vertical stitches 105(1) and 105(3) respectively, will indicate that the most common height is the height of the vertical stitches. These vertical stitches also include lower portions.

Height histogram 108 can be used to generate a height difference map that will represent the difference between the most common height and the height of each point of portion 101. Such a height difference map will indicate that vertical stitches 104(1)-104(5) are height differentiated narrow features. Accordingly, during a scan of portion 101 the focus error correction unit of system can operate either at an open loop-it generated focus error correction signals that ignore focus error signals generated while scanning vertical stitches 104(1)-104(5), or at closed loop, changing the expected value of the focus error signal in that area. Focus error correction unit 9 can extrapolate the areas that were scanned before reaching each of these vertical stitches.

It is noted that vertical stitch 105(2) is included within two slices 102($n$-1) and 102($n$). Slice 102($n$-1) includes both vertical stitch 105(2) and horizontal stitches 104(1)-104(5) thus its height reflects a weighted average height of about 0.30 micron.

Figure 5:
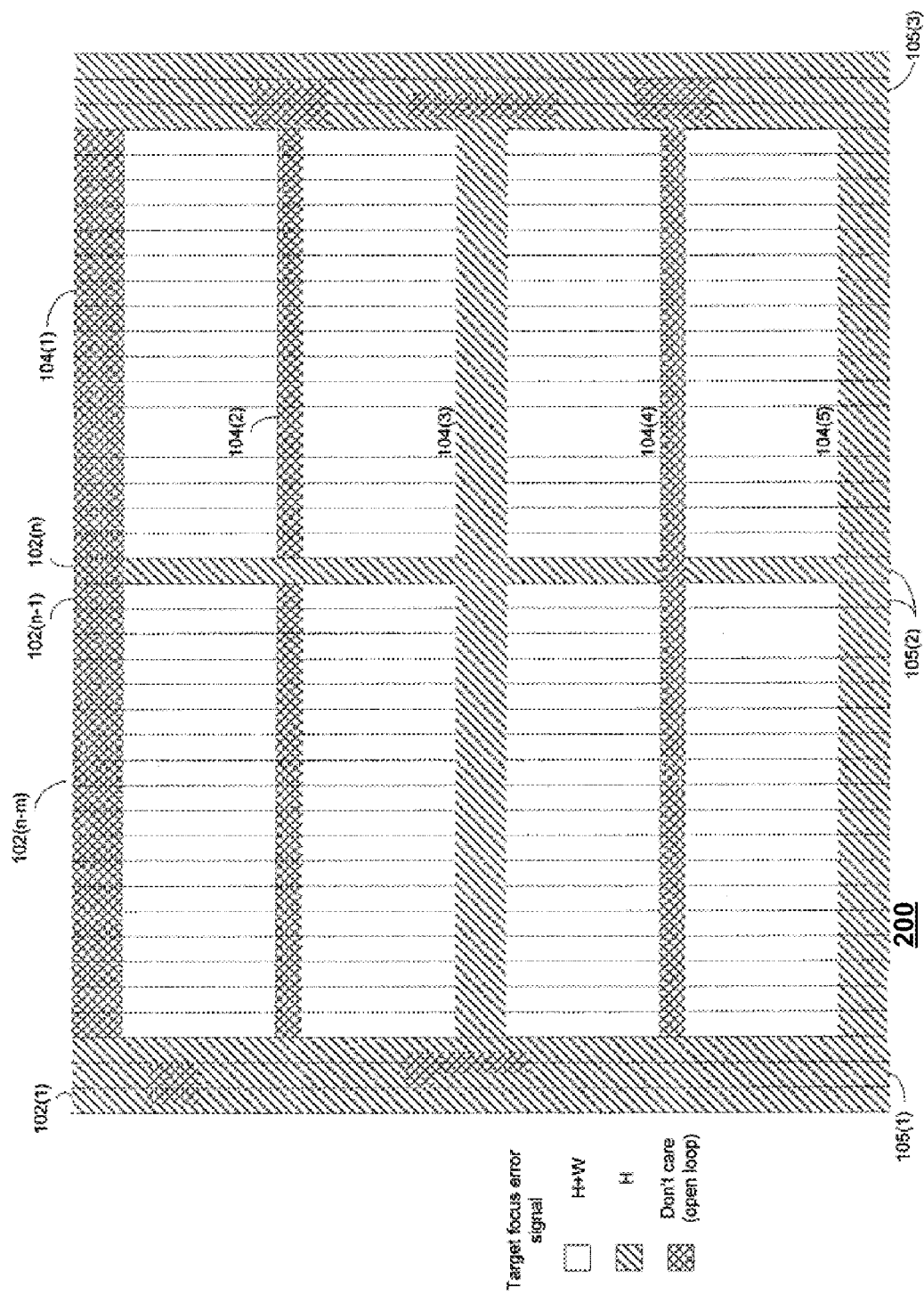
FIG. 5 illustrates a focus error correction map, according to an embodiment of the invention.

FIG. 5 illustrates a focus error correction map 200, according to an embodiment of the invention. Focus error correction map 200 includes multiple "don't care" zones in which the focus error correction unit will operate at an open loop and ignore focus error signals. The location of the "don't care" zones correspond to the locations of horizontal stitches 104(1)-104(5) as well as to some lower portions of vertical stitches 105(1) and 105(3).

It is noted that focus error correction map 200 can also indicate the target focus error signal at each location of the inspected object or a portion of the inspected object. If, for example, assuming that the height difference between a stitch and its surroundings is H and that the height of substantially transparent layer 1" at locations above any stitch is W, then the height of substantially transparent layer 1" over a memory cell is about (H+W)—(see also FIG. 4).

Accordingly, focus error correction unit 9 should define a target focus error signal that represents a focus error of W at locations above stitches and a target focus error signal of (H+W) at locations above memory cells. Thus, focus error correction unit 9 will not aim to minimize the focus error correction signal (and focus the system to a focal plane that corresponds to the upper surface of reflective layer 1") but rather try to focus on the surface of substantially transparent layer 1', thus tracking a substantially flat layer, at a given height.

Conveniently, focus error correction map 200 includes multiple pixels of a first size. This size corresponds to a first optical configuration (for example magnification) of system 1 when portion was scanned. It is noted that in some cases the optical configuration of system 1 differs from the first optical configuration. In many cases the first optical configuration is characterized by a pixel size that is smaller than the pixel size used while inspecting the inspected object.

When a focus error correction of a different pixel size (referred to as second pixel size) is required then system 1 and especially controller 24 convert focus error correction map 200 while taking into account the different pixel sizes.

The conversion can also take into account the different reflectivity of the height differentiated narrow feature (such as stitches) and of the surroundings of the height differentiated narrow feature. For example, assuming that the second pixel size is larger than the first pixel size. In this case the new (converted) focus error correction map will be generated by performing a weighted average of pixels to convert focus error correction map 200. The weighted averaging will try to assign a different weight to pixels of the memory cells and a different weight to pixels of stitches. The weight is conveniently, inversely proportional to the reflectivity of the stitches and of the memory cells, since the more the specific part reflects, the greater is its contribution towards the focus error signal.

It is noted that the focus error correction map 200 can include a map of a single die and that other dice of wafer 2 will be scanned according to that map, but this is not necessarily so. A focus error correction map can include only a portion of a die (for example one or more slices) as well as more than a single die.

It is noted that the system can perform map conversions even if the original map and the converted map have the same pixel size. This can occur when the scan plan changes. The system can perform a conversion in such a case by converting a first focus error correction map that comprises pixels of a first size to a second focus error correction map that comprises pixels of the first size. The conversion is responsive to possible spatial displacement between the pixels and to a relationship between a reflectivity of the height differentiated narrow feature and a reflectivity of a surroundings of the height differentiated narrow feature.

Figure 6:
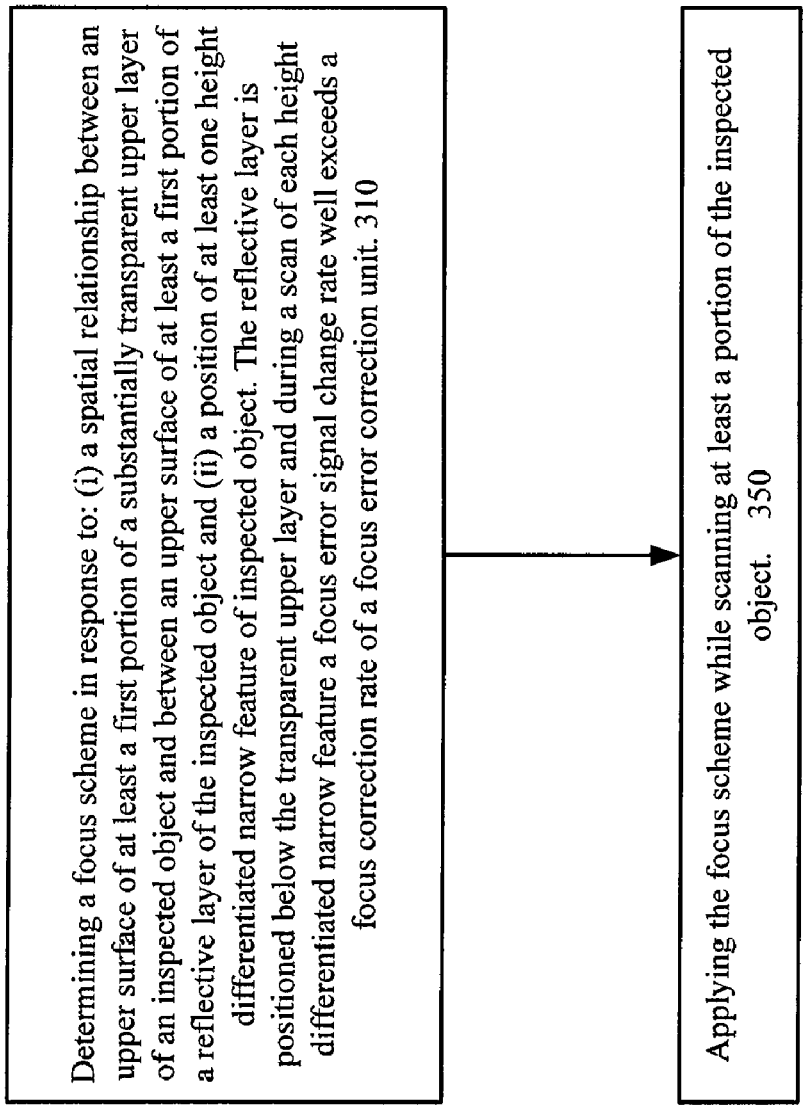
FIG. 6 is a flow chart illustrating a method for focus correction according to various embodiments of the present invention.

FIG. 6 illustrates method 300 for focus error correction, according to an embodiment of the invention.

Method 300 starts by stage 310 of determining a focus scheme in response to: (i) a spatial relationship between an upper surface of at least a first portion of a substantially transparent upper layer of an inspected object and between an upper surface of at least a first portion of a reflective layer of the inspected object and (ii) a position of at least one height differentiated narrow feature of inspected object. The reflective layer is positioned below the transparent upper layer and during a scan of each height differentiated narrow feature a focus error signal change rate well exceeds a focus correction rate of a focus error correction unit.

A height differentiated narrow feature can be a high patterned element, a deep trench, a scribe line, an edge of a wafer, and the like. The height differentiated narrow feature is characterized by a height profile that includes at least one rapidly changing height. It is noted that the width of the height differentiated narrow feature can be determined in view of the scanning rate and focus error correction rate of the system. Thus, slower scanning rates and alternatively or additionally, faster focus error correction rates can reduce the width of what can be regarded as a narrow feature.

According to an embodiment of the invention, stage 310 includes: (i) repetitively scanning the first portion of the substantially transparent upper layer and the first portion of the reflective layer; wherein during these repetitive scans focus error signals (from multiple locations) are obtained and stored; and (ii) defining, at these multiple locations, target focus error signals that may differ from zero, in response to the obtained focus error signals. The repetitive scanning can increase the signal to noise ratio of the focus error signals by averaging out random noise.

Conveniently, stage 310 includes scanning multiple areas of the inspected object and generating reflected layer height statistics representative of the distribution of heights of multiple locations of each area. A height of a certain point of the reflected layer can be obtained from a focus error signal generated in response to light reflected from that certain point as well as the position of a stage that holds the inspected object.

These statistics can include a height histogram of reflective layer 1". The height can be represented by focus error signals as well as the position of the stage that holds the inspected object. The stage is moved by the motor.

Conveniently, at least one scanned feature is defined as a height differentiated narrow feature in response to the statistics. Usually, features that are characterized by a height that strongly deviates from the average (or otherwise representative) height of a certain area, and are relatively narrow can be regarded as height differentiated narrow features, which may be ignored in the scan. If the height differentiated features are wide, such as horizontal stitch 104(3) in FIG. 5, their central part can be tracked with an appropriate value for the target focus error signal. For example, referring to FIG. 5, the central part of the horizontal stitch would have a target focus error signal of H.

Stage 310 may also include converting a first focus error correction map that includes pixels of a first size to a second focus error correction map that includes pixels of a second size. The conversion may be required, for example, if the first map was obtained with a first magnification factor while the method will apply the focus scheme while the optics use another magnification factor. The converting is responsive to a relationship between the first size and the second size and to a relationship between a reflectivity of the height differentiated narrow feature and a reflectivity of a surroundings of the height differentiated narrow feature. The reflectivity of the height differentiated narrow features is higher and even much higher than the reflectivity of its surroundings. Accordingly, when performing the map conversion this reflectivity should be taken into account.

Stage 310 is followed by stage 350 of applying the focus scheme while scanning at least a portion of the inspected object.

Conveniently, stage 350 includes at least one of the following stages, or a combination of two of more of the following stages: (i) Ignoring focus error signals generated while scanning the at least one height differentiated narrow feature; (ii) Determining focus error correction signals, when scanning a height differentiated narrow feature, in response to focus error corrections signals obtained from an area proximate to the height differentiated narrow feature, i.e., ignoring the focus error of the narrow feature. This can include performing an interpolation of the surface of the area scanned before reaching the height differentiated narrow feature; (iii) Determining focus error correction signals, when scanning a height differentiated narrow feature, in response to an expected shape of the height differentiated narrow feature. Thus, the shape (especially the height profile) of the height differentiated narrow feature can be known in advance, from previous scans of other (or the same) height differentiated narrow feature, from the design database used for manufacturing the inspected object, and the like. (iv) Determining target focus error signals at multiple locations, in response to spatial relationships between the substantially transparent upper layer and the reflective layer at these multiple locations.

According to an embodiment of the invention stage 350 includes selectively masking light reflected from at least a portion of a height differentiated narrow feature, before reaching a focus error correction unit. This masking can be useful in cases where scanned area (for example a strip) includes a part of a height differentiated narrow feature as well as its surroundings. For example, if the scanning pattern includes scanning vertical strips, and if a certain strip includes a portion of a vertical height differentiated narrow features (eg. vertical stitch) as well as its surroundings (eg. Cell) then by masking the surrounding portion, the focus error correction unit will receive light from the narrow features only (stitch), and can thus generate a focus error signal from a unique (not mixed) area (stitch) and thus succeed to focus the system onto the appropriate height. That is, using a target focus error signal for the specific masked slice which is matched to the unique height differentiated feature, e.g., in the case of a slice which has a vertical stitch in it, and this vertical stitch is the only part which is not masked, the appropriate target focus error signal would be 0.5 micron (if the vertical stitch was say 105(3) in the appropriate slice). By using a configurable spatial filter, mixed height differentiated narrow features positioned at different locations can be effectively masked, leaving a single well defined feature to "track".

It is noted that a focus error correction map can be altered while maintaining the same pixel size. Thus the method can include converting a first focus error correction map that comprises pixels of a first size to a second focus error correction map that comprises pixels of the first size. The converting is responsive to possible spatial displacement between the pixels and to a relationship between a reflectivity of the height differentiated narrow feature and a reflectivity of a surroundings of the height differentiated narrow feature.

While the present invention has been described with respect to certain exemplary embodiments, it is not limited thereto, and the full scope of the present invention is defined in the appended claims, as interpreted in accordance with applicable law.

We claim:

1. A method for focus error corrections: the method comprises:
   determining a focus scheme in response to:
      a spatial relationship between an upper surface of at least a first portion of a substantially transparent upper layer of an inspected object and an upper surface of at least a first portion of a reflective layer of the inspected object; wherein the reflective layer is positioned below the transparent upper layer, and
      a position of at least one height differentiated narrow feature of inspected object; wherein during a scan of each height differentiated narrow feature a focus error signal change rate well exceeds a focus correction rate of a focus error correction unit; and
   applying the focus scheme while scanning at least a portion of the inspected object.

2. The method according to claim 1 wherein the applying comprises ignoring focus error signals generated while scanning the at least one height differentiated narrow feature.

3. The method according to claim 1 wherein the applying comprises determining focus error correction signals, when scanning a height differentiated narrow feature, in response to focus error corrections signals obtained from an area proximate to the height differentiated narrow feature.

4. The method according to claim 1 wherein the applying comprises determining focus error correction signals, when scanning a height differentiated narrow feature, in response to an expected shape of the height differentiated narrow feature.

5. The method according to claim 1 wherein the determining a focus scheme comprises determining target focus error signals at multiple locations, in response to spatial relationships between the substantially transparent upper layer and the reflective layer at these multiple locations.

6. The method according to claim 1 wherein the determining a focus scheme comprises repetitively scanning the first portion of the substantially transparent upper layer and the first portion of the reflective layer; and in response to focus error signals obtained during the scanning defining, at multiple locations, target focus error signals that differ from zero.

7. The method according to claim 1 wherein the applying comprises selectively masking light reflected from at least a portion of a height differentiated narrow feature, before reaching a focus error correction unit.

8. The method according to claim 1 wherein the determining comprises scanning multiple areas of the inspected object and generating reflected layer height statistics representative of the distribution of heights of multiple locations of each area.

9. The method according to claim 8 further comprising defining at least one scanned feature as a height differentiated narrow feature in response to the statistics.

10. The method according to claim 1 further comprising converting a first focus error correction map that comprises pixels of a first size to a second focus error correction map that comprises pixels of a second size; wherein the converting is responsive to a relationship between the first size and the second size, and to the possible spatial displacement between the pixels.

11. The method according to claim 10 wherein the converting is further responsive to a relationship between a reflectivity of the height differentiated narrow feature and a reflectivity of a surroundings of the height differentiated narrow feature.

12. The method according to claim 1 further comprising converting a first focus error correction map that comprises pixels of a first size to a second focus error correction map that comprises pixels of the first size; wherein the converting is responsive to possible spatial displacement between the pixels and to a relationship between a reflectivity of the height differentiated narrow feature and a reflectivity of a surroundings of the height differentiated narrow feature.

13. A system having focus error corrections capabilities, the system comprises a controller and a scanner;

wherein the controller is adapted to determine a focus scheme in response to:
- a spatial relationship between an upper surface of at least a first portion of a substantially transparent upper layer of an inspected object and an upper surface of at least a first portion of a reflective layer of the inspected object; wherein the reflective layer is positioned below the transparent upper layer, and
- a position of at least one height differentiated narrow feature of the inspected object; wherein during a scan of each height differentiated narrow feature a focus error signal change rate well exceeds a focus correction rate of a focus error correction unit of the system; and wherein the controller is adapted to apply the focus scheme while the scanner scans at least a portion of the inspected object.

14. The system according to claim 13 wherein the controller is adapted to ignore focus error signals generated while when the scanner scans at least one height differentiated narrow feature.

15. The system according to claim 13 wherein the controller is adapted to determine focus error correction signals, when the scanner scans a height differentiated narrow feature, in response to focus error signals obtained from an area proximate to the height differentiated narrow feature.

16. The system according to claim 13 wherein the controller is adapted to determine focus error correction signals, when the scanner scans a height differentiated narrow feature, in response to an expected shape of the height differentiated narrow feature.

17. The system according to claim 13 wherein the controller is adapted to determine target focus error signals at multiple locations, in response to spatial relationships between the substantially transparent upper layer and the reflective layer at these multiple locations.

18. The system according to claim 13 wherein the system is adapted to determine a focus scheme by repetitively scanning a first portion of the substantially transparent upper layer and a first portion of the reflective layer and to define, at multiple locations, target focus error signals that differ from zero.

19. The system according to claim 13 wherein the system comprises a spatial filter adapted to selectively mask light reflected from at least a portion of a height differentiated narrow feature, before reaching the focus error correction unit.

20. The system according to claim 13 wherein the system is adapted to scan multiple areas of the inspected object and generate reflected layer height statistics representative of the distribution of heights of multiple locations of each area.

* * * * *